United States Patent
Smith (12)

(10) Patent No.: US 6,380,429 B1
(45) Date of Patent: Apr. 30, 2002

(54) PREPARATION OF SULFONYL IMINE COMPOUNDS

(75) Inventor: Eric Maurice Smith, Wilmington, DE (US)

(73) Assignee: E. I. du Pont Nemours and Company, Wilmington, DE (US)

( * ) Notice: Subject to any disclaimer, the term of this patent is extended or adjusted under 35 U.S.C. 154(b) by 0 days.

(21) Appl. No.: 09/663,737

(22) Filed: Sep. 15, 2000

Related U.S. Application Data

(60) Provisional application No. 60/156,361, filed on Sep. 28, 1999.

(51) Int. Cl.$^7$ .................. G07C 303/40; C07D 221/00; C07D 307/52; C07D 333/20; C07D 205/04
(52) U.S. Cl. .................. 564/87; 546/192; 548/561; 548/952; 549/75; 549/408; 549/495; 558/452; 562/553; 562/576; 564/89; 564/92; 564/463
(58) Field of Search ................ 564/87, 89, 92, 564/463; 549/75, 408, 495; 548/561, 952; 546/192; 562/553, 576; 558/452

(56) References Cited

U.S. PATENT DOCUMENTS 5,698,744 A    12/1997   Lee .................. 568/322

OTHER PUBLICATIONS

Ross A. Lee and Dennis S. Donald, An Efficient, Magnetically Retrievable and Recyclable Oxidant, Tetrahedron Letters, vol. 38, No. 22, pp. 3857–3860, 1997.

Alma Viso, et al., Sulfur–Directed Asymmetric 1,3–Dipolar Cycloadditions of Azomethine Ylides with Enantiopure Sulfinimines, J. Org. Chem, 62, pp. 2316–2317, 1997.

Franklin A. Davis, et al., Asymmetric Synthesis and Properties of Sulfinimines (Thiooxaime S–Oxides), J. Org. Chem, 62, pp. 2555–2563, 1997.

Fukuyama, et al. 2– and 4–Nitrobenzenesulfonamides: Exceptionally Versatile Means for Preparation of Secondary Amines and Protection of Amines, Tetrahedron Letters, vol. 36, No. 36, pp. 6373–6374, 1995.

Steven M. Weinreb, N–Sulfonyl Imines—Useful Synthons in Stereselective Organic Synthesis, Topics in Current Chemistry, vol. 190, pp. 131–184, 1997.

*Primary Examiner*—Peter O'Sullivan

(57) ABSTRACT

Disclosed is a process for the oxidation of sulfonamides to sulfonyl imines using chromium (IV) dioxide as the oxidant.

15 Claims, No Drawings

PREPARATION OF SULFONYL IMINE COMPOUNDS

This application claims profit, benefit of U.S. Provisional application No. 60/156,361, filed Sep. 28, 1999, now expired.

FIELD OF THE INVENTION

This invention concerns a process for the oxidation of sulfonamides to sulfonyl imines using chromium (IV) dioxide as oxidant.

TECHNICAL BACKGROUND OF THE INVENTION

There are no known routes to sulfonyl imines of the structure $R_1R_2C=NSO_2R_3$ via oxidation of the corresponding sulfonamides.

S. M. Weinreb, *Topics in Current Chemistry*, Volume 190, 131–184 broadly reviews the preparation and chemical reactions of N-sulfonyl imines.

F. A. Davis et al., *J. Org. Chem.*, 1997,62, 2555–2563 disclose processes for the preparation of enantiomerically pure sulfinimines.

A Viso et al., *J. Org. Chem.*, 1997, 62, 2316–2317 discuss the cycloaddition reactions of sulfinimines.

T. Fukuyama et al., *Tetrahedron Letters*, Vol. 36, No. 36, pp. 6373–6374 report the preparation of 2- and 4-nitrobenzenesulfonamides and their use as amine protective groups with easy chemical removal by thiolates.

R. A. Lee and D. S. Donald, *Tetrahedron Letters*, vol. 38, No. 22, pp. 3857–3860, 1997 disclose the utility of Magtrieve® chromium dioxide as an oxidant for the conversion of alcohols to aldehydes and ketones.

U.S. Pat. No. 5,698,744 discloses the utility of chromium dioxide for a variety of oxidation processes. Oxidation of alcohols and activated hydrocarbons are exemplified.

There is a need for a process for the oxidation of sulfonamides to corresponding sulfonyl imines.

SUMMARY OF THE INVENTION

This invention discloses the use of chromium dioxide as a suitable oxidizing agent for the preparation of sulfonyl imines. The use of chromium (IV) dioxide provides the advantage of using magnetism to separate residual chromium from the desired product.

Also disclosed is a process for the oxidation of sulfonamide of the structure I

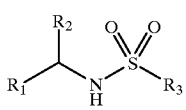

I where $R_1$ and $R_2$ are independently selected from the group consisting of hydrogen and organic radicals not possessing a hydrogen atom in the position beta to the nitrogen of the sulfonamide group; and $R_3$ is an organic radical selected from the group consisting of alkyl, substituted alkyl, aryl, and substituted aryl groups, and optionally, $R_1$ and $R_2$ can form a ring, to sulfonyl imines of the structure II,

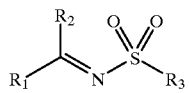

II wherein $R_1$, $R_2$, and $R_3$ are as described above, said process comprising:

(a) optionally, contacting a sulfonamide of the structure I with a suitable solvent or liquid;

(b) contacting the sulfonamide of the structure I with chromium (IV) dioxide under oxidizing conditions whereby a sulfonyl imine product is produced; and (c) optionally, isolating the sulfonyl imine product.

Another disclosure of the present invention is a process for the preparation and in-situ use of imines of the structure III,

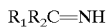

$R_1R_2C=NH$   III from corresponding sulfonyl imines of the structure II

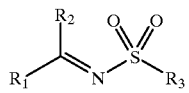

II having iminyl functionality and wherein $R_1$ and $R_2$ are independently selected from the group consisting of hydrogen and organic radicals not possessing a hydrogen atom in the position beta to the nitrogen of the sulfonamide group, and wherein $R_3$ is an organic radical selected from the group consisting of alkyl, substituted alkyl, aryl, and substituted aryl groups, and optionally, $R_1$ and $R_2$ can form a ring, comprising:

(a) contacting the sulfonyl imine of the structure II with a reagent that is capable of reacting with the iminyl functionality of the structure II to form a derivative of structure III having a sulfonyl group; and (b) removing the sulfonyl group.

A further disclosure of the present invention is a process for the preparation and in-situ use of a combinatorial library of imines of the structure III,

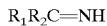

$R_1R_2C=NH$   III from corresponding sulfonyl imines of the structure II

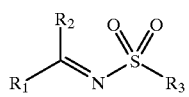

II having iminyl functionality and wherein $R_1$ and $R_2$ are independently selected from the group consisting of hydrogen and organic radicals not possessing a hydrogen atom in the position beta to the nitrogen of the sulfonamide group, and wherein $R_3$ is an organic radical selected from the group consisting of alkyl, substituted alkyl, aryl, and substituted aryl groups, and optionally, $R_1$ and $R_2$ can form a ring, comprising:

(a) contacting the sulfonyl imines of the structure II with one or more reagents that are capable of reacting with the iminyl functionality of the structure II to form at least one derivative of structure III having a sulfonyl group; and (b) removing the sulfonyl group.

DETAILED DESCRIPTION OF THE INVENTION

This invention relates to a process for the oxidation of sulfonamides to produce sulfonyl imines. The invention lies in the use of chromium (IV) dioxide ($CrO_2$) to afford yields which are generally greater than 50% and purities greater than 70% under reaction conditions that are relatively easy to carry out.

One source of chromium (IV) dioxide is E. I. du Pont de Nemours and Company, Wilmington, Del., which sells the material under the trade name Magtrieve®. Magtrieve® is a recyclable magnetic chromium (IV) dioxide.

In the process of the present invention,

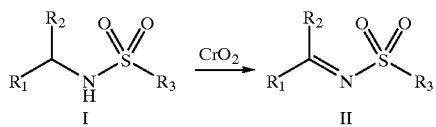

the sulfonamides of the structure I and resulting sulfonyl imine products of the structure II may bear a wide variety of organic substituents. $R_1$ and $R_2$ are selected from the group consisting of hydrogen and organic radicals not possessing a hydrogen atom in the position beta to (i.e., 2 carbon atoms away from) the nitrogen of the sulfonamide group. $R_1$ and $R_2$ may be hydrogen, alkyl, alkenyl, substituted alkyl or alkenyl, alkynyl, and aryl, including phenyl, substituted aryl and heteroaryl, and optionally, $R_1$ and $R_2$ can together form a ring. Preferably, $R_1$ and $R_2$ are selected from the group consisting of hydrogen, optionally, substituted aryl and optionally, substituted heterocyclic groups. Specifically exemplified $R_1$ and $R_2$ substituents are hydrogen, phenyl, p-fluorophenyl, p-methoxyphenyl, 2-furanyl, and 2-thiophenyl.

$R_3$ is an organic radical selected from the group consisting of alkyl, substituted alkyl, aryl, and substituted aryl groups. Specifically exemplified $R_3$ substituents include 2-nitrophenyl, 2,4-dinitrophenyl, p-tolyl, p-methoxyphenyl, methyl, and trifluoromethyl.

The sulfonamide of the structure I may be prepared by contacting an amine of the structure $R_1R_2CHNH_2$ wherein $R_1$ and $R_2$ are independently selected from the group consisting of hydrogen and organic radicals not possessing a hydrogen atom in the position beta to the nitrogen, with a sulfonyl chloride of the structure $R_3SO_2Cl$. Other methods known in the art may be used also.

Sulfonyl imines may be prepared by the process disclosed at temperatures from about 20° C. to about 200° C., preferably from about 50° C. to about 200° C., and most preferably from about 100° C. to about 130° C.

The process is most conveniently carried out at atmospheric pressure. Super- or sub-atmospheric pressure may be used if desired.

The process can be carried out with the sulfonamide at least partially dissolved in a suitable solvent or liquid. A wide variety of solvents or liquids may be used. Suitable solvents and liquids are aprotic, non-nucleophilic liquids that are unreactive to the chromium dioxide oxidation reagent under reaction conditions. Preferred solvents and liquids are aromatic hydrocarbons (for example, benzene or toluene), substituted benzenes (for example, chlorobenzene or dichlorobenzene), halogenated aliphatic hydrocarbons (for example, carbon tetrachloride and dichloroethane), acetonitrile, nitromethane, esters, and ethers.

The reaction mixture is heterogeneous. Agitation by means customary in the art is acceptable.

Upon conclusion of the reaction, particulate chromium dioxide is conveniently removed from the liquid organic substrate/solvent phase by filtration, centrifugation or magnetic separation.

The process of this invention is useful in the synthesis of organic compounds (specifically sulfonyl imines). These compounds have utility as intermediates in the synthesis of further compounds and in combinatorial chemistry techniques.

The present invention also discloses a process for the in situ use of N-unsubstituted imines of the structure III, $$R_1R_2C=NH \qquad \text{III}$$

wherein $R_1$ and $R_2$ are independently selected from the group consisting of hydrogen and organic radicals not possessing a hydrogen atom in the position beta to the nitrogen of the sulfonamide group. N-unsubstituted imines often are unstable and cannot be isolated for use in further reactions. The process and in situ use is defined to mean generating, in effect, an N-unsubstituted imine that is protected by a sulfonyl group. This protected imine is used in the desired reaction. Optionally, the product is then deprotected by the removal of the sulfonyl group to produce the desired final product.

The process comprises (a) contacting the sulfonyl imines of the structure II with one or more reagents that are capable of reacting with the iminyl functionality of the structure II to form at least one derivative of structure III having a sulfonyl group and (b) removing the sulfonyl group.

A suitable reaction is one in which an N-unsubstituted imine will react with the reagent to form the desired product wherein the sulfonyl group is inert to all other reagents and solvents used under the reaction conditions. The optional deprotection step can be any performed method known in the art. By "deprotection" is meant the step in which the sulfonyl group is removed.

To illustrate, one specific example is a [4+2] cycloaddition reaction where $R_3$ is a nitro-substituted benzene substituent. Addition of ammonia to aldehydes and ketones does not form stable N-unsubstituted imine adducts. Trimers or other polymers are formed instead. In this example, a nitro- or dinitrobenzenesulfonyl imine serves as the synthetic equivalent of an N-unsubstituted imine. After subsequent reactions, nitro- and dinitro- sulfonamide groups, which are stable to acids and bases, are efficiently removed using nucleophilic reagents, for example thiols and primary amines, including polymer supported nucleophiles (e.g. polymer supported thiols and amines).

An added feature of the sulfonyl imine protecting group in this example is the electron withdrawing property of the aromatic ring. The methine CH of a nitro- or dinitro-benzenesulfonyl imine is significantly more electrophilic and more reactive than the methine CH of other imines.

The above-described process of the cycloaddition/ deprotection is illustrated below.

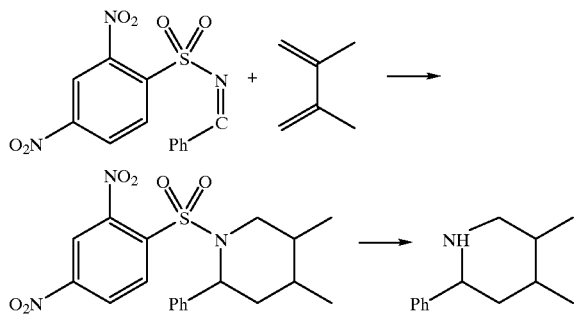

Since the process described above is facile, performed under mild conditions requiring no catalyst, and results in purities generally over 70%, it may be used to generate and utilize a combinatorial library of N-unsubstituted imines by using one or more of the sulfonamides of the structure I to produce one or more sulfonyl imine products of structure II.

The process described is useful as an equivalent to obtain the desired product. The following reaction equation would be impossible to perform due to the instability of N-unsubstituted imine.

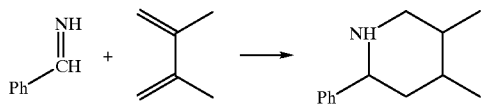

Another example of processes of the instant invention is detailed below, wherein $R_1$, $R_2$, $R_3$, $R_4$, and $R_5$ are hydrogen, alkyl, alkenyl, substituted alkyl or alkenyl, alkynyl, and aryl, including phenyl, substituted aryl, and heteroaryl, and optionally, $R_1$ and $R_2$ can form a ring, and wherein Nuc indicates a nucleophilic group Such as, but not limited to, a thiol, a primary or secondary amine, a Grignard reagent, a phosphine, and a halogen.

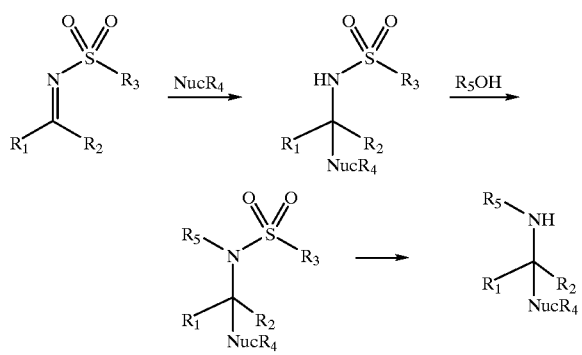

This reaction also lends itself well to combinatorial processes and the creation of a combinatorial library.

Additional reactions in which the sulfonyl imine of structure II can be substituted for the imine of structure III that can be used in the processes of the instant invention include, but are not limited to, nucleophilic additions, [2+2] cycloadditions, and ene reactions to form β-amino acids, α-aminonitriles, amines, cyclic amines, and β-lactams among others illustrated below and described in Weinreb, ibid.

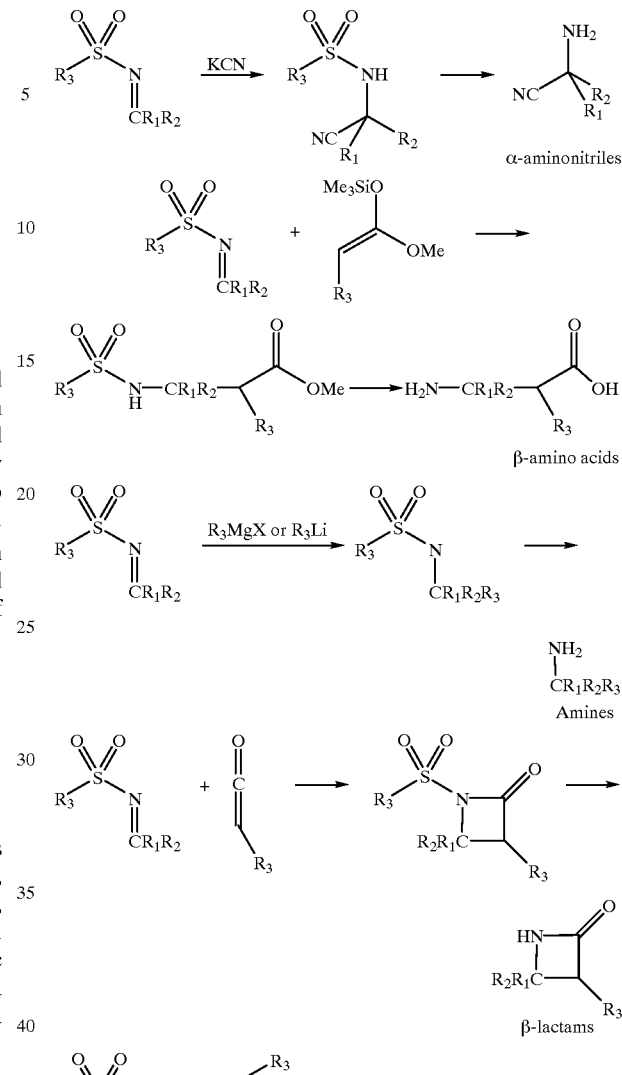

All of these reactions can he adapted to combinatorial processes and the creation of a combinatorial library as well.

As used herein, a combinatorial library is an intentionally created collection of a plurality of differing molecules which can be prepared by selected synthetic means and screened for the desired activity or characteristic in a variety of formats (e.g., libraries of soluble molecules, libraries of compounds attached to resin beads, silica chips, or other solid supports). The libraries are generally prepared such that the compounds are approximately in equimolar quantities, and are prepared by combinatorial syntheses. Combinatorial syntheses refers to the parallel syntheses of diverse compounds by sequential additions of multiple choices of reagents which leads to the generation of large chemical libraries containing related molecules having molecular diversity. Screening methods for libraries vary greatly and are dependent upon desired activity, size of library, and class of compounds in the library.

The libraries of the instant invention can be of any type. These types include, but are not limited to, arrays and mixtures. Arrays are libraries in which the individual compounds are simultaneously synthesized in spatially segregated locations, typically identified by their location on a grid. Mixture libraries contain a mixture of compounds that are simultaneously synthesized and assayed. Identification of the most active compound is then performed by any of several techniques well known in the combinatorial art (for example, deconvolution).

EXAMPLES

General Procedures. Sulfonamides used herein were prepared from commercially available amines and sulfonyl chlorides by standard techniques known in the art.

Example 1
Preparation of sulfonyl imine: $4\text{-}CH_3OC_6H_4CH\!=\!N\text{-}SO_2C_6H_3(2,4\text{-}diNO_2)$ Under an inert atmosphere, a 20-mL shell vial fitted with a Teflon® fluoropolymer lined cap was charged with 50 mg of the 2,4-dinitrobenzene-sulfonamide derivative of 4-methoxybenzylaminesulfonamide, 500 mg chromium(IV) dioxide (Magtrieve® 30 $m^2/g$, obtained from Aldrich, Milwaukee, Wis.), and 5 mL anhydrous chlorobenzene. After shaking 14 h. at 250 rpm and 110° C. on a platform orbital shaker, the reaction mixture was filtered to remove $CrO_2$ and concentrated by rotary evaporation to afford 43 mg of sulfonyl imine $4\text{-}CH_3OC_6H_4CH\!=\!N\text{-}SO_2C_6H_3(2,4\text{-}diNO_2)$ (86% yield). Purity, as determined by $^1H$ NMR was >98%.

The other Examples in Table 1 were carried out using the same general procedure. Entries in the first column were carried out using Magtrieve® chromium dioxide obtained from Aldrich, having a surface area of 56 $meter^2/g$. Entries in the third column of the Table are comparative examples and were carried out using the same general procedure as above except that manganese dioxide was used as the oxidizing agent.

TABLE 1

| EXAMPLES Desired sulfonyl imine structure | Using $CrO_2$ (56 $m^2/g$) | | Using $CrO_2$ (30 $m^2/g$) | | Using $MnO_2$ | |
|---|---|---|---|---|---|---|
| | Mass recovery | Purity of desired sulfonyl imine structure | Mass recovery | Purity of desired sulfonyl imine structure | Mass recovery | Purity of desired sulfonyl imine structure |
| PhCH=N-SO$_2$-C$_6$H$_3$(2,4-diNO$_2$) | 79% | >98% | 89% | >98% | 13% | 0% |
| PhCH=N-SO$_2$-C$_6$H$_4$(2-NO$_2$) | 86% | >98% | N/A | N/A | N/A | N/A |
| PhCH=N-SO$_2$-C$_6$H$_4$(4-CH$_3$) | 74% | >98% | N/A | N/A | 36% | ~90% |
| PhCH=N-SO$_2$-C$_6$H$_4$(4-OCH$_3$) | 72% | >98% | N/A | N/A | N/A | N/A |
| PhCH=N-SO$_2$-(2,2,5,7,8-pentamethylchroman-6-yl) | 70% | >98% | 83% | >90% | 51% | >90% |

TABLE 1-continued

| EXAMPLES<br>Desired sulfonyl imine structure | Using CrO$_2$ (56 m$^2$/g) | | Using CrO$_2$ (30 m$^2$/g) | | Using MnO$_2$ | |
|---|---|---|---|---|---|---|
| | Mass recovery | Purity of desired sulfonyl imine structure | Mass recovery | Purity of desired sulfonyl imine structure | Mass recovery | Purity of desired sulfonyl imine structure |
| PhCH=N-SO$_2$-CH$_3$ | 80% | >98% | N/A | N/A | N/A | N/A |
| PhCH=N-SO$_2$-CF$_3$ | 17% | 43% | 4% | 0% | 8% | 0% |
| 4-H$_3$CO-C$_6$H$_4$-CH=N-SO$_2$-(2,4-dinitrophenyl) | 74% | >98% | 86% | >98% | N/A | N/A |
| Ph$_2$C=N-SO$_2$-(2,4-dinitrophenyl) | 90% | 60% | N/A | N/A | N/A | N/A |
| (2-thienyl)-CH=N-SO$_2$-(2,4-dinitrophenyl) | 57% | >98% | 70% | 74% | 28% | <50% |
| (2-furyl)-CH=N-SO$_2$-(2,4-dinitrophenyl) | 32% | >95% | 68% | 45% | N/A | N/A |
| 4-F-C$_6$H$_4$-CH=N-SO$_2$-(2,4-dinitrophenyl) | 84% | >98% | 98% | >98% | N/A | N/A |

What is claimed is:

1. A process for the oxidation of sulfonamide of the structure I

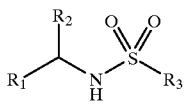

where $R_1$ and $R_2$ are independently selected from the group consisting of hydrogen and organic radicals not possessing a hydrogen atom in the position beta to the nitrogen of the sulfonamide group, and $R_3$ is an organic radical selected from the group consisting of alkyl, substituted alkyl, aryl and substituted aryl groups, and optionally, $R_1$ and $R_2$ can form a ring, to sulfonyl imines of the structure II,

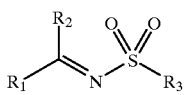

wherein $R_1$, $R_2$, and $R_3$ are described above, said process comprising:

(a) optionally, contacting a sulfonamide of the structure I with a suitable solvent or liquid;

(b) contacting the sulfonamide of the structure I with chromium (IV) dioxide under oxidizing conditions whereby a sulfonyl imine product is produced; and (c) optionally, isolating the sulfonyl imine product.

2. The process of claim 1 wherein the $R_1$ and $R_2$ substituents of the sulfonamide of structure I are selected from the group consisting of hydrogen, optionally, substituted aryl, and optionally, substituted heterocyclic groups.

3. The process of claim 2 wherein the $R_1$ and $R_2$ substituents of the sulfonamide of structure I are selected from the group consisting of hydrogen, phenyl, p-fluorophenyl, p-methoxyphenyl, 2-furanyl, and 2-thophenyl.

4. The process of claim 1 wherein the $R_3$ substituent of the sulfonamide of structure I is selected from the group consisting of 2-nitrophenyl, 2,4-dinitrophenyl, p-tolyl, p-methoxyphenyl, methyl, and trifluoromethyl.

5. The process of claim 1 wherein the sulfonamide is contacted with chromium (IV) dioxide at temperatures from about 50° C. to about 200° C.

6. The process of claim 4 wherein the temperature is from about 100° C. to about 130° C.

7. The process of claim 1 wherein the sulfonamide is contacted with the chromium (IV) dioxide at atmospheric pressure.

8. The process of claim 1 wherein the sulfonyl imine is isolated by magnetically removing residual chromium.

9. The process of claim 8 wherein the suitable liquid is selected from the group consisting of aromatic hydrocarbons, substituted benzenes, halogenated aliphatic hydrocarbons, acetonitrile, nitromethane, esters, and ethers.

10. A process for the preparation and in situ use of imines of the structure III,

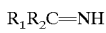

from corresponding sulfonyl imines of the structure II

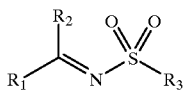

having iminyl functionality and wherein $R_1$ and $R_2$ are independently selected from the group consisting of hydrogen and organic radicals not possessing a hydrogen atom in the position beta to the nitrogen of the sulfonamide group, and wherein $R_3$ is an organic radical selected from the group consisting of alkyl, substituted alkyl, aryl and substituted aryl groups, and optionally, $R_1$ and $R_2$ can form a ring, comprising:

(a) contacting the sulfonyl imine of the structure II with a reagent that is capable of reacting with the iminyl functionality of the structure II to form a derivative of structure III having a sulfonyl group; and (b) removing the sulfonyl group.

11. The process of claim 10 wherein the sulfonyl group removed in step (b) is replaced with a hydrogen.

12. The process of claim 10 wherein the sulfonyl imine of the structure II is prepared from corresponding sulfonamides of the structure I,

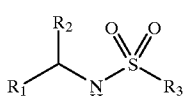

comprising:

(a) optionally, contacting the sulfonamide of the structure I with a suitable liquid;

(b) contacting at least one sulfonamide of structure I with chromium (IV) dioxide under oxidizing conditions whereby a sulfonyl imine product of the structure II is produced;

(c) optionally, isolating the products having the structure II produced in step (b).

13. A process for the preparation and in-situ use of a combinatorial library of imines of the structure III,

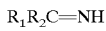

from corresponding sulfonyl imines of the structure II

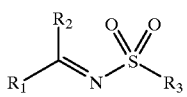

having iminyl functionality and wherein $R_1$ and $R_2$ are each independently selected from the group consisting of hydrogen and organic radicals not possessing a hydrogen atom in the position beta to the nitrogen of the sulfonamide group, and wherein $R_3$ is an organic radical selected from the group consisting of alkyl, substituted alkyl, aryl, and substituted aryl groups, and optionally, any of $R_1$ and $R_2$ can form a ring, comprising:

(a) contacting the sulfonyl imines of the structure II with one or more reagents that are capable of reacting with the iminyl functionality of the structure II to form at least one derivative of structure III having a sulfonyl group; and (b) removing the sulfonyl group.

14. The process of claim 13 wherein the sulfonyl group removed in step (b) is replaced with a hydrogen.

15. The process of claim 13 wherein the sulfonyl imines of the structure II are prepared from corresponding sulfonamides of the structure I,

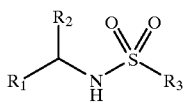

I comprising:

(a) optionally, contacting at least one sulfonamide of the structure I with a suitable liquid;

(b) contacting at least one sulfonamide of structure I with chromium(IV) dioxide under oxidizing conditions whereby a sulfonyl imine product of the structure II is produced;

(c) optionally, isolating the products having the structure II produced in step (b).

* * * * *